US00PP08237P

United States Patent [19]

Tucker

[11] Patent Number: Plant 8,237

[45] Date of Patent: May 25, 1993

[54] PEACH TREE NAMED TUCKER'S

[76] Inventor: Joseph H. Tucker, 2500 E. Sophi La., Kingsburg, Calif. 93631

[21] Appl. No.: 704,218

[22] Filed: May 22, 1991

[51] Int. Cl.[5] ..... A01H 5/00

[52] U.S. Cl. ..... Plt./43.2

[58] Field of Search ..... Plt./43, 43.2

[56] References Cited

U.S. PATENT DOCUMENTS

P.P. 4,398 3/1979 Merrill ..... Plt. 43

*Primary Examiner*—James R. Feyrer

*Attorney, Agent, or Firm*—Bernhard Kreten

[57] ABSTRACT

A peach tree which is of medium size, open density, vigorous, spreading upright, foliated with medium size, lanceolate, abruptly pointed leaves having a serrulate margin, both globose and reniform glands and the stipules are long on mature foliage, blooms early to medium with a large size which is conical in shape and flattening at full bloom, showing, pink large flowers, and a very productive bearer of average, uniform, oblate very rounded, very late ripening freestone fruit having golden yellow with red blush skin, and yellow to cherub orient pink flesh, the surface of the pit cavity being red. The fruit ripens substantially after the last commercial variety presently grown.

2 Drawing Sheets

DISCOVERY OF THE VARIETY

The present new and distinct variety of peach tree was observed some distance from the inventor's orchard growing as a volunteer in the inventor's yard of his home. The inventor observed the tree blooming and fruiting uncharacteristically and took particular note of the late ripening period and the prolonged duration of time the fruit remains on the tree when ripe.

ASEXUAL REPRODUCTION OF THE VARIETY

A number of plants of the present variety were asexually reproduced by budding; the work was performed under a contract between the inventor and a commercial nursery. Clones of the original seedling were identical to the parent plant in every distinguishing characteristic.

SUMMARY OF THE VARIETY

The present variety of peach tree is, characteristically, of medium size, excellent vigor, with an open, spreading upright structure; foliated in medium quantity lanceolate, abruptly pointed leaf having a medium serrate margin and mixed glands of both globose and reniform type; blooms mid-season with showy pink flowers up to 2¼" diameter and apparently self fertile and producing abundant pollen. The tree is a high yield, productive bearer of a heavy well set crop of medium sized peaches of the free stone variety having yellow, extremely firm, non-melting flesh and red coloration around the pit. The skin color is golden yellow with a red blush over approximately 50% of the skin area. The skin possesses a light pubescence.

The tree is a vigorous grower, the original tree exhibiting approximately eight feet of top growth in one year. The trunk texture is slightly rough; the branch texture is smooth on one-year old wood, changing to slightly rough in the second year growth. Pruning methods and cultivation practices basically determine tree size and shape.

The tree blooms in early March in the San Joaquin Valley. Flower buds are light pink, conical shaped which flatten out at full bloom. Internode length varies from average to slightly less than average. The fruit begins to size quickly in late September or early October resulting in very late ripening from October 22nd onward.

During the last two weeks of maturation the red blush becomes pronounced and the fruit continues to size well (2½" to 2¾" average diameter). The ripe fruit hangs well on the tree into November. The initiation of dormancy, as indicated by yellowing leaves and leaf fall, is delayed on the instant peach until the crop has matured and is removed from the tree.

BRIEF DESCRIPTION OF THE DRAWING

Sheet 1 of the drawing, top color photograph, shows a flowering stem in peak bloom stage with numerous open blossoms in various stages of maturity. The photograph also shows the bark color of fruiting wood, internodes, bud scale scars, and vegetative buds of such wood. The bottom color photograph depicts a typical stem of the tree having mature, late season foliage; three whole fruit of the variety in various positions to depict the exterior color and the shape of fruit at harvest stage; and, one fruit split along the suture to show flesh color, stone pit color, the stone, and the surface characteristics of the stone.

Sheet 2 of the drawing shows the shape of a mature specimen of the tree in full bloom before foliation. This photograph also shows the character and strength of the trunk, color and surface texture characteristics of mature bark of the variety of this disclosure; the branching habit of the tree and the shape of a mature specimen of the tree.

DESCRIPTION OF THE VARIETY

The following is a detailed description of the variety of peach tree growing under the ecological condition prevailing near Porterville, Tulare County, Calif. Color references are to the Maerz and Paul Dictionary of Colors except where terminology having generally accepted meaning is employed.

Tree:

*Size.*—Medium.

*Density.*—Open.

*Vigor.*—Vigorous.

Trunk:

*Size.*—6¾" diameter (5 year old tree).

*Texture.*—Slightly rough.

Branches:

*Size (lateral).*—Range ½"-2½" diameter.

*Texture.*—Smooth on first year growth changing to slightly rough on second year growth.

*Branching habit.*—Spreading upright.

*Lenticels.*—Numerous.

*Color.*—Brown to grayish brown.

Foliage:

*Quantity.*—Medium.

Leaves:

*Size.*—Medium.

*Shape.*—Lanceolate, abruptly pointed.

*Length.*—115 to 120 mm.

*Width.*—37 to 41 mm.

*Thickness.*—Less than 1 mm.

*Texture.*—Smooth.

*Margin.*—Serrulate.

*Petiole.*—10 mm.

*Glands.*—Mixed, both globose and reniform.

*Stipules.*—Two present ½" long on mature foliage, early deciduous.

*Color.*—Underneath surface — (plate 23, page 69 J-6) cedar green. Upper leaf surface — (plate 23, page 69 L-5) mt. vernon green.

Flower bud:

*Size.*—1⅛" in length×½" diameter.

*Shape.*—Conical, flattening at full bloom.

Flowers:

*Size.*—Large: up to 2¼" diameter.

*Color.*—Showy pink, large.

Bloom:

*Date of full bloom.*—March 15th to March 18th.

*Anthers.*—yellowish brown on red stamens.

Fruit:

*Maturity.*—When described — shipping firm ripe. Date of first picking — Oct. 22, 1990. Date of last picking — Nov. 29, 1990.

*Size.*—Average diamter-2¾".

*Uniformity.*—Very uniform sizing.

*Form.*—Oblate very rounded.

*Suture.*—Slight indentation.

*Ventral surface.*—Uniformly round; 2⅞"-3" diameter.

*Cavity.*—Unsplit pits filled cavities.

*Base.*—Uniform concave, very slight cleavage.

*Apex.*—Rounded, slightly pointed.

Skin:

*Thickness.*—Average.

*Tendency to crack.*—No cracking.

*Color.*—Golden yellow with a red blush. Base-(plate 9, E-8) ceres. Blush (plate 5, G-11) fujiyama.

*Down or hairiness.*—Light pubescence.

Flesh:

*Color.*—Yellow (plate 9, H-6) cherub orient pink, red aroung the pit (plate 7, L-8) mascara.

*Juice.*—Slight when picked increasing slightly off tree.

*Texture.*—Very firm, non-melting.

*Amygdalin.*—Absent.

*Flavor.*—Sweet with mildly subacid.

*Aroma.*—Slight to moderate.

*Eating quality.*—Excellent.

Stone:

*Adherence to flesh.*—Freestone.

*Size.*—1⅜" length×⅝" width×11/16" thickness.

*Form.*—Elliptical.

*Hilum.*—Oval Shaped 1/32" deep×3/16" long×⅛" wide.

*Dorsal edge.*—Slightly arched.

*Ventral edge.*—Pendulous and rounded.

*Surface.*—Rough, deeply fissured.

*Color.*—Reddish brown.

*Tendency to split.*—No split pits ever found.

Use: fresh market.

Keeping quality: excellent.

Shipping quality: excellent.

Resistance to insects: No unusual susceptibilities noted.

Resistance to disease: No unusual susceptibilities noted.

Fruit and foliage has withstood temperatures down to 30° F.

Although this novel variety of peach tree possesses the described characteristics under the ecological conditions at Porterville, Tulare County, Calif. (lat. 36°05', long 119°00', elev. 455' above sea level) at the southern portion of the San Joaquin Valley, it is to be understood that variation in these characteristics incident to differing climatic and soil condition and cultural practices are anticipated.

I claim:

1. A new and distinct very late ripening variety of a freestone peach tree having flesh of the yellow variety substantially as herein shown and described, having fruit of good to high, excellent sugar content, being of medium size, yellow in color with a red blush, being firm and not melting, and by having a desirable oblate shape, where the peach ripens substantially after other late harvest existing commercial varieties, typically in later October and in November.

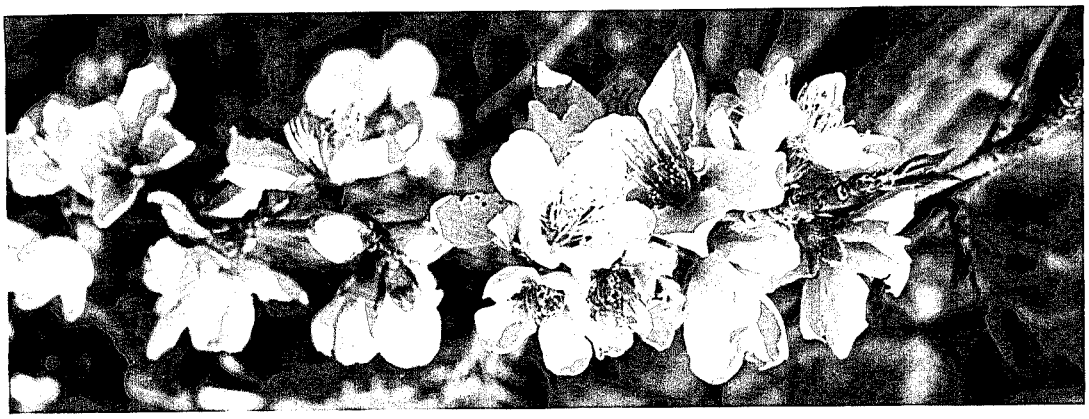
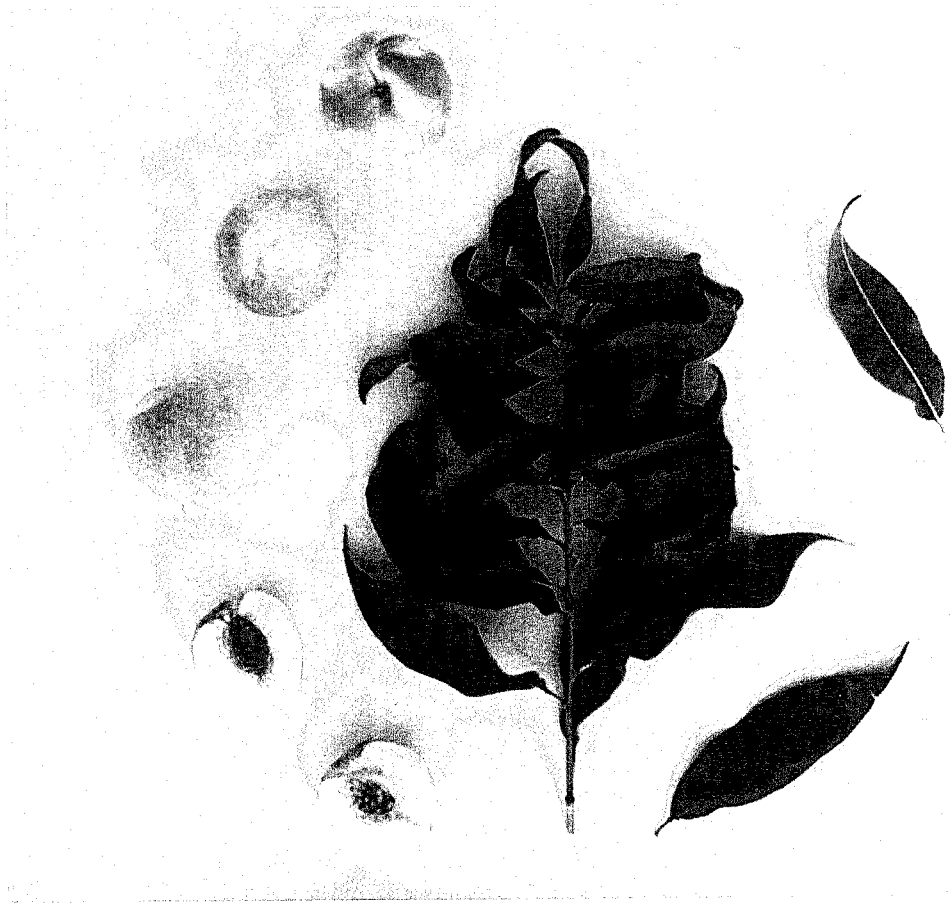

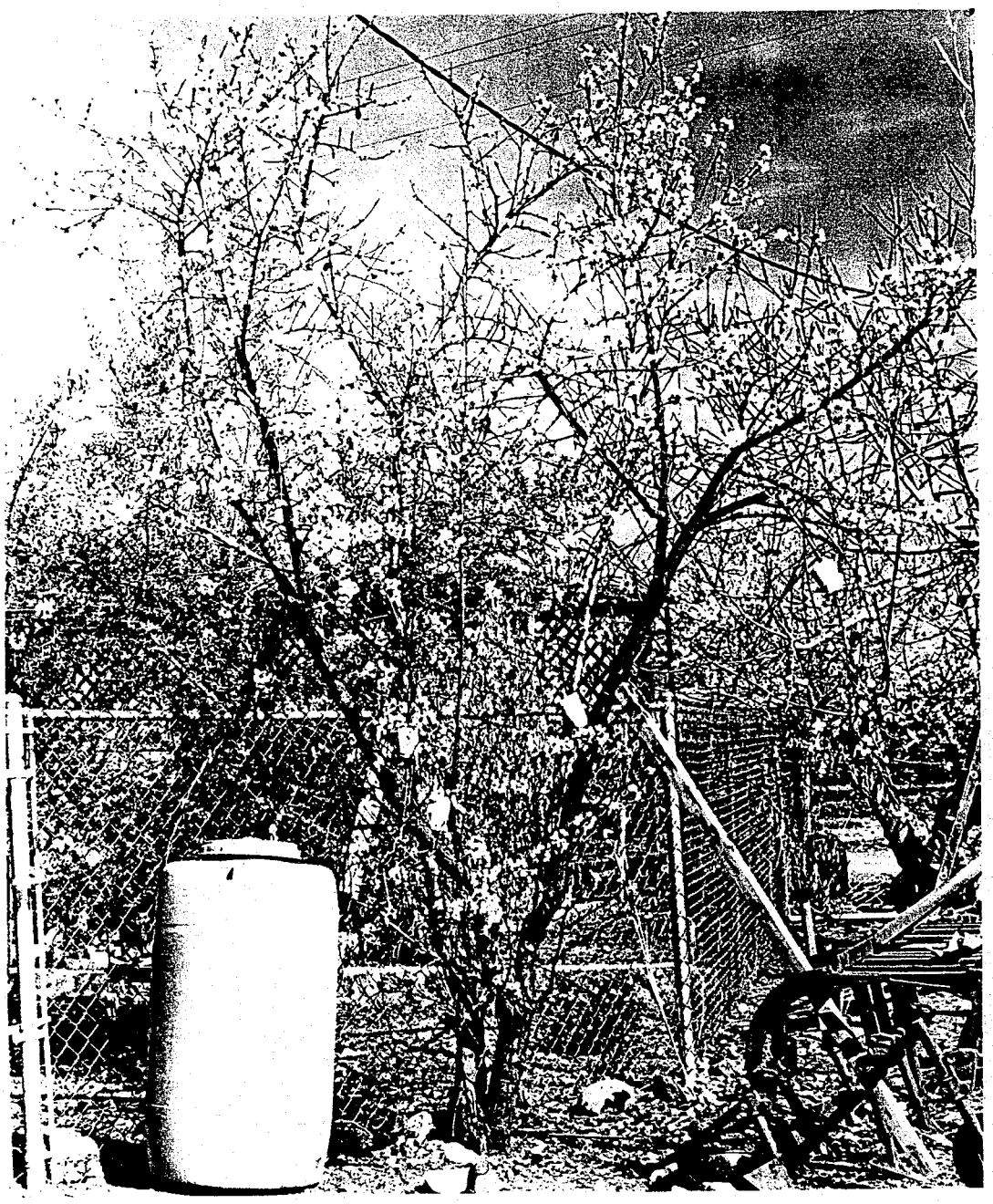

* * * * *